US005540700A

United States Patent [19]
Rowden et al.

[11] Patent Number: 5,540,700
[45] Date of Patent: Jul. 30, 1996

[54] UTERINE MANIPULATOR

[75] Inventors: Jimmy M. Rowden; Kerry L. Blair, both of Olathe, Kans.

[73] Assignee: The Cooper Companies, Fort Lee, N.J.

[21] Appl. No.: 237,142

[22] Filed: May 3, 1994

Related U.S. Application Data

[63] Continuation-in-part of Ser. No. 106,521, Aug. 16, 1993, Pat. No. 5,409,496.

[51] Int. Cl.⁶ ............................. A61B 17/42; A61B 17/46
[52] U.S. Cl. ............................................. 606/119; 600/201
[58] Field of Search ......................... 604/55, 164, 264, 604/282, 283; 606/1, 119, 108, 190, 193, 198; 600/201, 204, 213

[56] References Cited

U.S. PATENT DOCUMENTS

| | | |
|---|---|---|
| 1,856,295 | 5/1932 | Sovatkin . |
| 2,186,143 | 1/1940 | Neugass . |
| 2,456,806 | 12/1948 | Wolffe . |
| 3,131,690 | 5/1964 | Innis et al. . |
| 3,153,267 | 10/1964 | Cowland, Jr. . |
| 3,196,865 | 7/1965 | Rose . |
| 3,749,088 | 7/1973 | Gauthier . |
| 3,766,909 | 10/1973 | Ozbey . |
| 3,877,433 | 4/1975 | Librach . |
| 3,948,270 | 4/1976 | Hasson . |
| 4,022,208 | 5/1977 | Valtchev . |
| 4,066,071 | 1/1978 | Nagel . |
| 4,085,756 | 4/1978 | Weaver . |
| 4,323,057 | 4/1982 | Jamieson . |
| 4,430,076 | 2/1984 | Harris . |
| 4,562,832 | 1/1986 | Wilder et al. . |
| 4,597,030 | 6/1986 | Brody et al. . |
| 4,627,421 | 12/1986 | Symbas et al. . |
| 4,775,362 | 10/1988 | Kronner . |
| 4,996,974 | 3/1991 | Ciarlei . |
| 4,997,419 | 3/1991 | Lakatos et al. . |
| 5,104,377 | 4/1992 | Levine . |
| 5,195,964 | 3/1993 | Kletzky et al. . |
| 5,232,443 | 8/1993 | Leach . |
| 5,237,985 | 8/1993 | Hodgson et al. . |
| 5,242,240 | 9/1993 | Gorham . |
| 5,273,026 | 12/1993 | Wilk . |
| 5,382,252 | 1/1995 | Failla et al. ........................... 606/119 |
| 5,429,619 | 7/1995 | Furnish ................................. 604/283 |

FOREIGN PATENT DOCUMENTS

2078526  1/1982  United Kingdom .

*Primary Examiner*—Gary Jackson
*Assistant Examiner*—Glenn Dawson
*Attorney, Agent, or Firm*—William Squire

[57] ABSTRACT

A uterine manipulator and associated tip are provided for laparoscopic examinations. The manipulator hereof includes a handle pivotally connected to one end of an elongated frame and a drum positioned at the other end of the frame. The handle is connected to the drum to provide movement of the drum in a plane substantially parallel to the pivot axis of the handle. The handle may be locked relative to the frame in a plurality of desired positions by engagement of a pawl shiftable with the handle in one of a plurality of notches on the frame. The frame is provided with ports along the sides to facilitate cleaning and sterilization. The tip is mounted exclusively remotely to the frame of the uterine manipulator and includes a unique mounting system which maintains the proper orientation of the tip on the drum.

23 Claims, 6 Drawing Sheets

UTERINE MANIPULATOR

This application is a continuation in part of application Ser. No. 08/106,521 filed Aug. 16, 1993, now U.S. Pat. No. 5,409,496 the contents of which are incorporated herein by reference.

BACKGROUND OF THE INVENTION

1. Field of the Invention

This invention concerns a medical instrument used to manipulate a uterus during laparoscopic examination or surgery and a method of use associated therewith. The instrument of the present invention is designed to receive a manipulating element or tip which may be moved relative to the frame of the instrument by turning a handle, the device hereof including a locking mechanism for holding the handle in a desired position relative to the frame.

2. Description of the Prior Art

Gynecologists must frequently examine the internal pelvic organs of a patient by using a laparoscope. The medical procedures necessitating the use of a laparoscope may include laparoscopic tubal occlusion and fertility studies. During such laparoscopic procedures, it is frequently necessary for the uterus to be repositioned relative to its conventional orientation within the patient's abdomen in order to obtain an X-ray photograph or to perform surgery.

Instruments have been developed to aid the surgical team in these procedures, and particularly to manipulate the uterus into a desired orientation. Typically, these instruments involve a tip or hook which is pivotally mounted on a frame and which can be manipulated by a handle of some type positioned remotely from the tip. The devices are used by inserting the tip through the vaginal canal until reaching the uterus. With the tip engaging the uterus, medical personnel shift a handle or the like on the portion of the device then exterior to the patient's body, which in turn raises the uterus into position. Such devices are shown by, for example, U.S. Pat. Nos. 4,022,208 to Valtchev, 4,085,756 to Weaver, and 5,237,985 to Hodgson et al.

These instruments have a common disadvantage in that they may fatigue the user because of weight of the instrument and the energy needed to maintain the tip in the desired angular relationship to the frame during laparoscopic procedures. Consequently, while using a handle which pivots about an axis substantially perpendicular relative to the frame is beneficial, it has heretofore presented problems with respect to user fatigue and longevity of use of the device.

There has thus developed a need for a lightweight uterine manipulation device which reduces user fatigue due to weight.

There has also developed a need for a uterine manipulation device which reduces the fatigue of the user by providing a means for locking the handle to retain the tip in a desired orientation relative to the frame and for improved leverage for turning the handle relative to the frame to reposition the uterus during the laparoscopic procedure.

There has further developed a need for a uterine manipulation device which is simplified, having a minimum number of parts.

There is also a need for a uterine manipulation device which provides improved durability for prolonged use, while remaining sufficiently economical as to be economically disposed after a single use.

There is a need for a uterine manipulator having an improved means for mounting a disposable tip and holding that tip in position.

There is a need for a uterine manipulator which may be more readily cleaned and sterilized for reuse.

There is a need for a uterine manipulator providing a greater range of articulation making the handle more accessible to the surgeon when manipulating the patient's uterus.

There is also a need for a uterine manipulator which may be readily supported when the user's hands must be freed for other events during the laparoscopic procedure.

SUMMARY OF THE INVENTION

These and other needs are advantageously met by the uterine manipulation device according to the present invention. The device hereof uniquely includes a selectively actuatable locking mechanism in connection with a handle pivotally mounted relative to the main frame. The locking mechanism effectively serves to position the tip mounted on the snap-drum of the frame, as the snap-drum is operatively connected to the handle. The snap-drum is further uniquely configured for receiving a uterus-engaging tip.

The invention hereof broadly includes a frame, a handle, a tip-carrying snap-drum, a locking member and control connections extending between the snap-drum and the handle. The invention also includes a uniquely configured tip for mounting on the snap-drum, the tip including a flexible mounting boot for wrapping around the snap-drum and a rod for holding the tip in a rigid orientation relative to the snap-drum.

In greater detail, the handle is generally L-shaped, including a graspable portion oriented generally perpendicular to the frame. The handle carries the locking mechanism, including a pawl normally biased toward engagement with the frame. The portion of the frame adjacent the handle is provided with a plurality of slots, enabling the handle to be positively locked into a desired orientation relative to the frame.

The handle is connected to the snap-drum by the control connection, which preferably includes a pair of wires attached to the handle and the snap-drum. By pivoting the handle, concomitant movement of the snap-drum is accomplished. The snap-drum is preferably not directly connected to the frame, but rather held in position between sidewalls of the frame and the aforementioned wires. To this end, the snap-drum does not have a pivot point but rather moves through a vertical range while changing the angle of orientation of a mounting bore and the tip received thereon relative to the frame.

The snap-drum and the tip present a unique configuration which provide easy insertion into the uterus while maintaining positive securement of the tip to the frame. The snap-drum includes a rounded drum surface which receives a boot of the complimentally configured tip therearound, thus provided enhanced engagement of the boot to the drum. Further, the drum includes a fin and slot engagement with the boot to inhibit rotation of the tip relative to the uterine manipulator during use.

The frame of the uterine manipulator is conveniently provided with access ports along the top, bottom and side surfaces to facilitate cleaning and sterilization of the device. Yet further, the handle is configured to pivotally mount to the frame by a pivot pin which is offset to the axis of the graspable portion of the handle, giving a greater mechanical advantage to the user when pivoting the handle to proved corresponding movement of the snap-drum and tip.

The snap-drum is not connected directly to the frame, and is constrained by the sidewalls of the frame to inhibit side to side movement of the snap-drum relative to the frame. The control wire, or more preferably wires, limit fore-and-aft movement of the snap-drum relative to the frame and at the same time cause the snap-drum to "float" through a range of angular motion when the handle is pivoted. In contrast to prior art uterine manipulators having only about a 110° range of articulation, the present invention permits the handle to be rotated so that the tip articulates through about a 140° range relative to the frame. The enhanced range of motion is largely attributable to the avoidance of any pivot point and a construction which permits the snap-drum to articulate without pivoting about a pivot point. The snap-drum thus does not include a pivot point, but rather moves relative to the frame both angularly and vertically.

These and other advantages of the present invention will be readily appreciated with reference to the drawing and description set forth below.

DESCRIPTION OF THE PREFERRED EMBODIMENT

Figure 3:
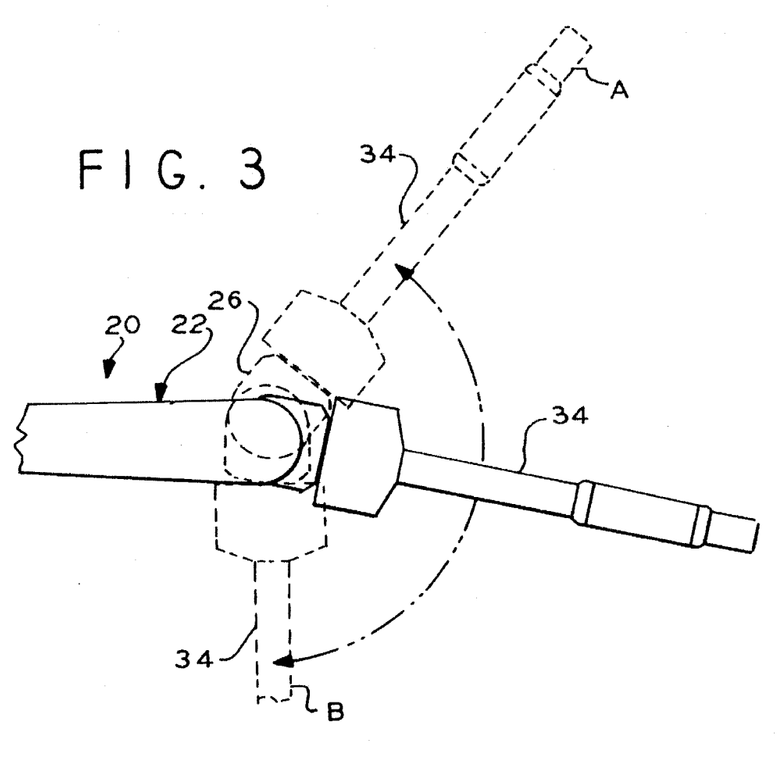
FIG. 3 is an enlarged, fragmentary side elevational view of the uterine manipulator hereof with a retractor tip mounted thereon, showing the range of angular movement of the tip in phantom.

Referring now to the drawing, a uterine manipulator 20 in accordance with the present invention broadly includes an elongated frame 22, a handle 24 pivotally coupled to one end thereof, a mounting snap-drum 26 positioned at the other end of the frame 22, a pivot pin 28 pivotally coupling the handle 24 and the frame, connecting means 30 extending along the frame 22 between the handle and snap-drum 26 for actuating movement of the snap-drum 26 through a desired angular range of motion, and a locking mechanism 32 for selectively locking the handle against undesired pivoting relative to the frame 22. As may be seen in FIG. 3, the snap-drum 26 is shiftable through a range of motion to retrovert and antevert a removable tip 34 mounted thereon when the handle 24 is pivoted about a the pivot pin 28.

In greater detail, the frame 22 is of a modified I-beam construction as shown in FIGS. 14 through 18 which includes a top wall 36, a bottom wall 38, sidewalks 40 and 42, upright beam 44, transverse beam 46, crossbrace 48 and upper brace 50 which serves to restrict and constrain the connecting means 30 within the frame. The top wall 36 and bottom wall 38 are substantially flat and provided with aligned holes 52 and 54 for receiving the pivot pin 28 therein, and are wider at the proximate end 56 than the narrower remote end 58 of the frame 22. As may be seen in FIG. 15, side access ports 60 and 62 are presented by the space between the top wall 36 and the bottom wall 38 on the proximate side of the transverse beam 46. Similarly, top access port 64 and bottom access port 66 are presented by the space between the side walls 40 and 42 on the remote side of the upright beam 44. The upright beam 44 interconnects the top wall 36 and the bottom wall 38 and is joined at a cruciform junction 68 with transverse beam 46 to support the frame 22. Similarly, transverse beam 46, crossbrace 48 and upper brace 50 interconnect sidewalls 40 and 42 and serve to maintain the sidewalls 40 and 42 in properly spaced-apart relationship for constraining the snap-drum 26 therebetween. Sidewalls 40 and 42 present a gradually increasing vertical dimension more proximate the remote end 58, as may be seen in FIG. 15. The frame 22 is preferably cast or otherwise formed of stainless steel, although rigid synthetic resin material could also be used to provide a more economical unit for single-use applications.

Figure 4:
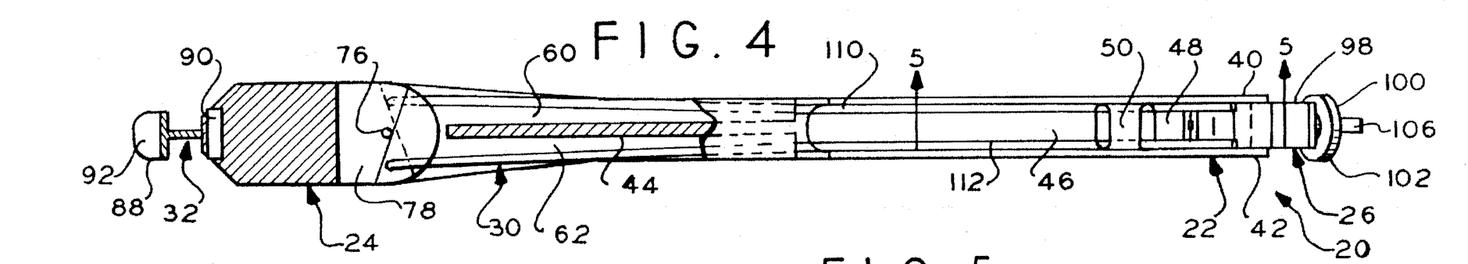
FIG. 4 is a top plan view similar to FIG. 2 but in partial section along line 4—4 of FIG. 1, showing parts of the frame, handle and control wires in phantom.
Figure 5:
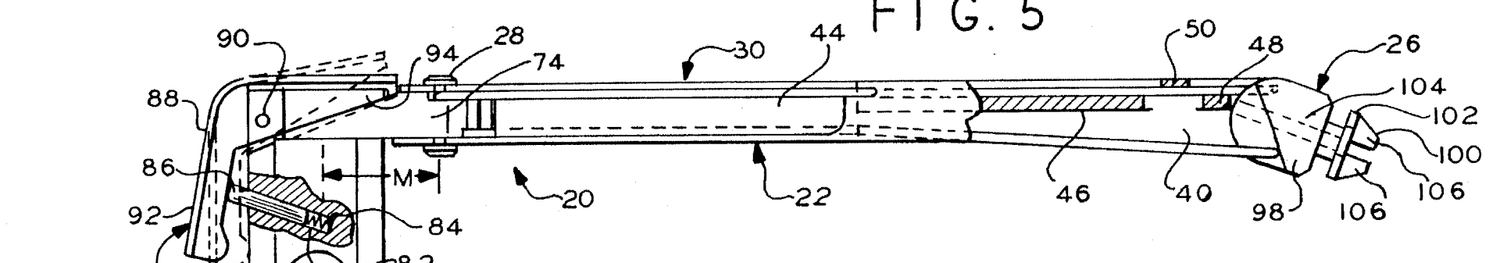
FIG. 5 is a side elevational view similar to FIG. 1, showing the disengaged position of the locking lever in phantom.

Handle 24 is preferably generally machined or alternatively molded of synthetic resin in an inverted L-shape, and is provided with a graspable section 70 defining a central opening 72 which both reduces weight and enables the user to pass a length of fabric or other supporting material therethrough to suspend the handle 24 during surgery. The handle further includes an arm 74 projecting from the graspable section 70 which includes an aperture 76 as seen in FIG. 4. The graspable section 70 is elongated and aligned with but offset from the aperture 76 adapted for connecting to the frame 22, thereby defining a moment arm M when the handle 24 is pivoted relative to the frame 22. The handle 24 includes a top relieved area 78 along the remote part of the arm 74 for permitting the connecting means 30 to swing through a desired range of motion, and a similar bottom relieved area 80 on the bottom side of the remote part of the arm 74. The graspable section 70 further includes a bore 82 opening toward the rear or proximate side of the uterine manipulator 20 for receiving spring 84 and rod 86 which serve in locking the handle in the desired position relative to the frame 22.

To that end, the rear or proximate end of the handle 24 mounts locking pawl 88 which is part of the locking mechanism 32. The pawl 88 is pivotally connected to the handle 24 by pin 90, the pawl 88 including a thumblatch 92 and catch 94. The thumblatch 92 is normally biased away from the handle 24 by rod 86 whereby the catch 94 engages a selected notch 96 on the proximate end of the frame 22. The pawl 88 is preferably molded of synthetic resin material.

Snap-drum 26 includes a flat-sided body 98 configured to fit between the sidewalls 40 and 42 of the frame 22 at the remote end 58 thereof, and a head 100 which projects outwardly from the body and includes a circular rim 102. The rim 102 preferably extends laterally about the width of the external sides of the sidewalls 40 and 42, as seen in FIG. 4. A channel 104 extends internally through the snap-drum 26 for receiving a portion of the tip 34 thereon. The head 100 also includes a fin 106 which projects generally in the remote direction from the rim 102 for engaging with a complemental surface on the tip 34. A neck 108 of reduced diameter connects the body 98 to the head 100, permitting enhanced connection of the tip 34 to the head 100.

The pivot pin 28 is preferably of metal such as stainless steel and may be a rivet or provided with a threaded fastener at one end to provide a secure connection between the handle and the frame.

Figure 6:
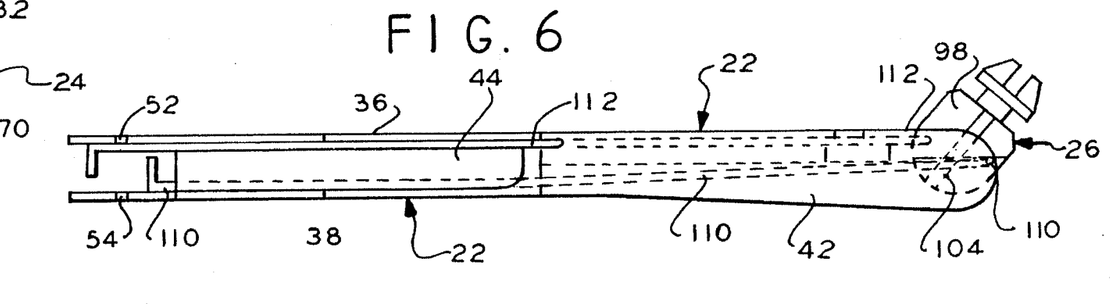
FIG. 6 is a fragmentary view of the frame with the handle removed, showing the position of the control wires during elevation of the snap-drum.
Figure 7:
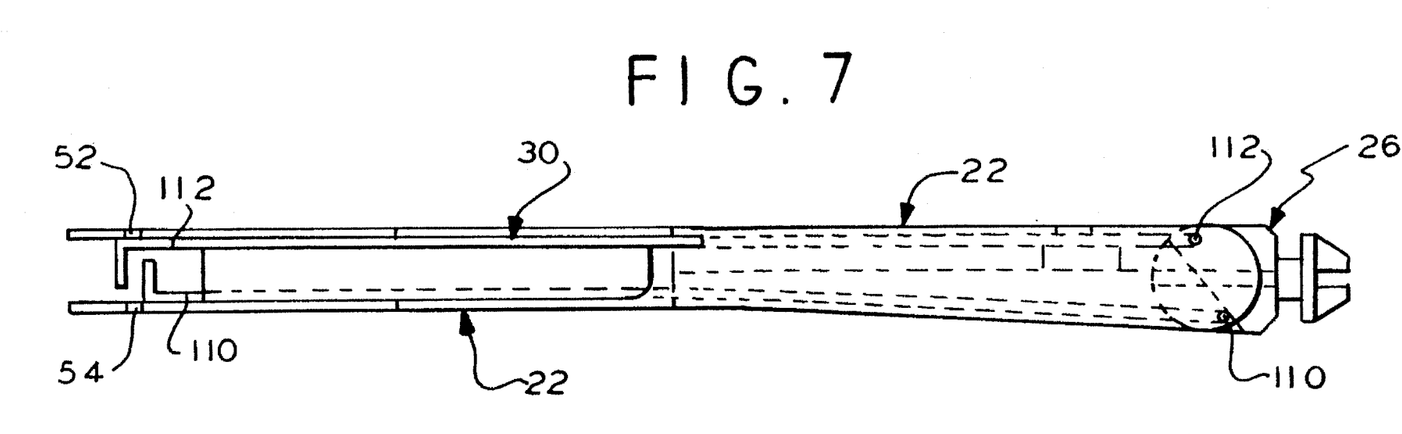
FIG. 7 is a fragmentary view similar to FIG. 6, showing the snap-drum in a neutral orientation in alignment with the frame.
Figure 8:
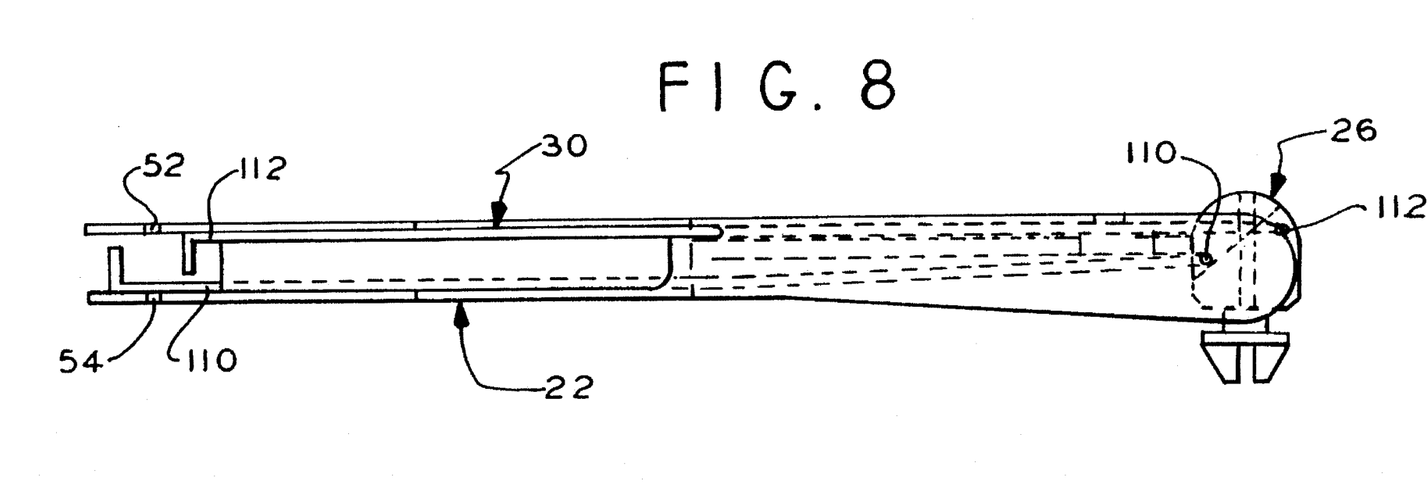
FIG. 8 is a fragmentary view similar to FIG. 7, showing the snap-drum in a depressed orientation.

The handle 22 and the snap-drum 26 are connected by connecting means 30, which preferably includes a pair of wires 110 and 112. The wires 110 and 112 are bent at the proximate and remote ends thereof to fit into corresponding holes in the arm 74 and body 98, respectively, the body 98 being provided with corresponding relieved areas on each side to permit movement of the snap-drum 26 without interference between the wires 110 and 112 and the sidewalls 40 and 42. As may be seen from FIGS. 6 through 8, the wires 110 and 112 are shifted longitudinally to initiate corresponding motion of the snap-drum 26, this being in turn caused by pivoting of the handle 24 about the axis defined by the pivot pin 28. Wire 110 extends along the length of the frame 22 whereby it is positioned above the transverse beam 46 and crossbrace 48 but below the top wall 36 and upper brace 50, and also to the left side of upright beam 44. Wire 112 extends along the length of the frame 22 and is positioned below the transverse beam 46 and crossbrace 48 but above the bottom wall 38, and to the right of upright beam 44. This arrangement provides good control and stability for the wires 110 and 112 while maintaining the desired separation between the wires and permits the wires to cause movement of the snap-drum only within the desired range of vertical motion.

Figures 1, 11:
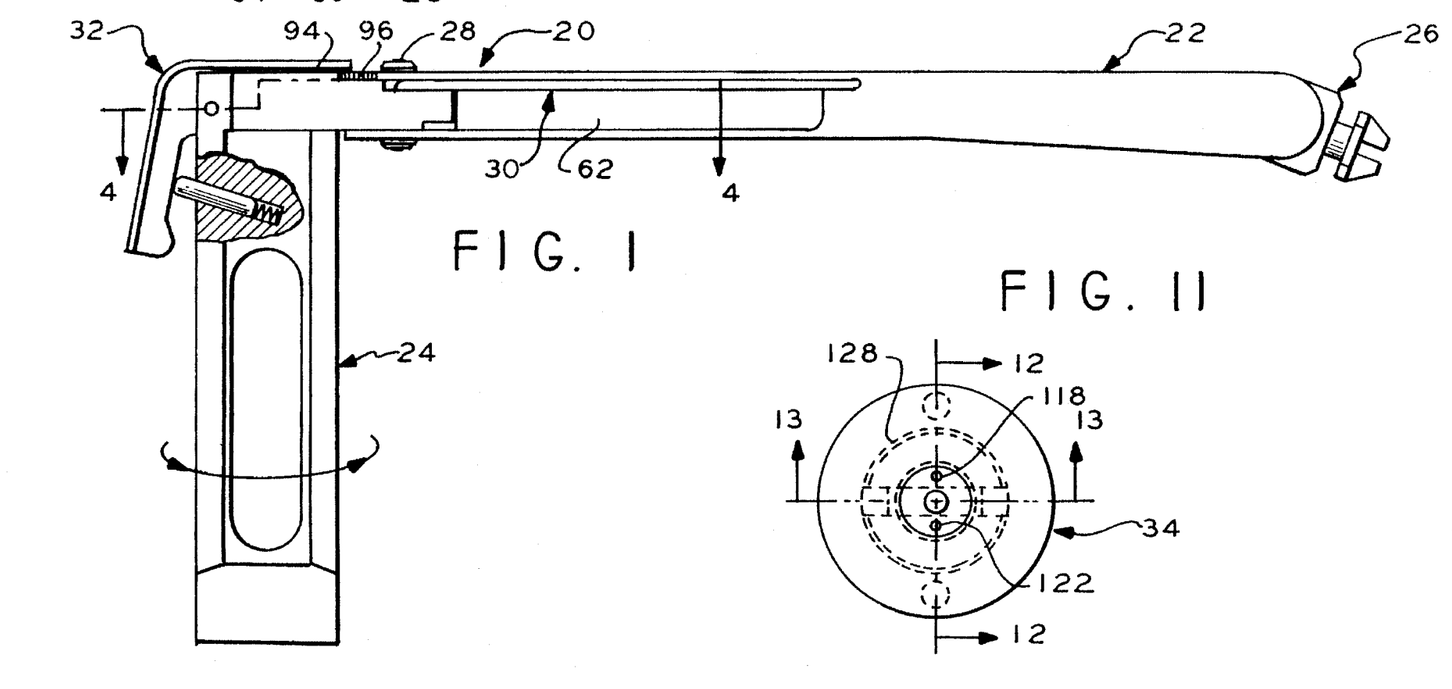
FIG. 1 is a right side elevational view of the uterine manipulator of the present invention, showing a portion of the handle containing part of the locking mechanism in section.
FIG. 11 is a front end elevational view of the tip hereof and shown in section through its shaft.
Figure 9:
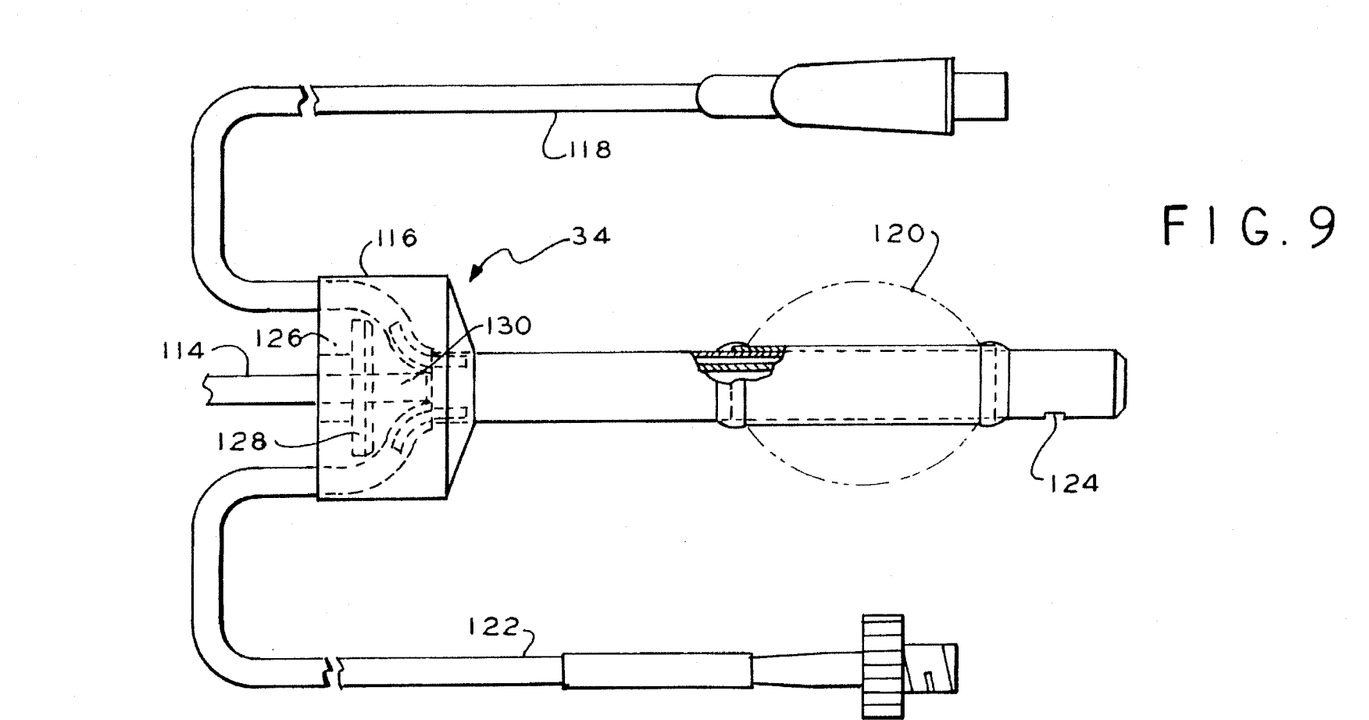
FIG. 9 is an enlarged side elevational view of the tip for mounting to the snap-drum of the uterine manipulator hereof, showing the balloon on the shaft of the tip in an inflated condition in phantom.
Figure 10:
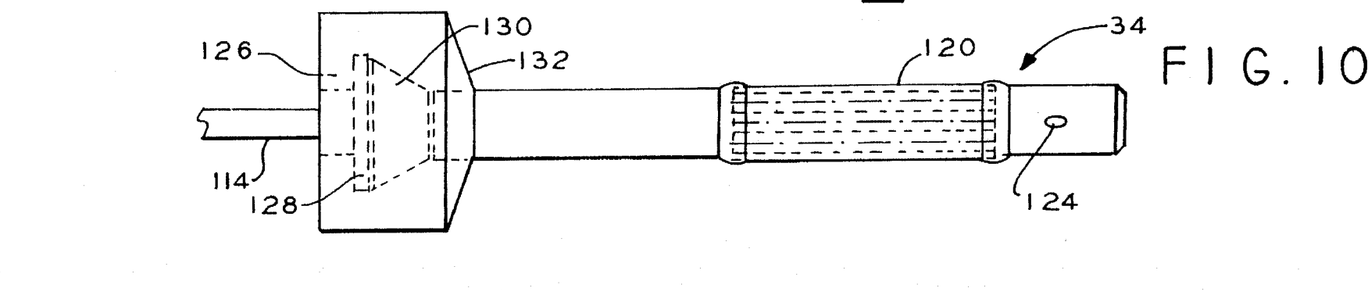
FIG. 10 is an enlarged top plan view of the tip of FIG. 9.
Figure 12:
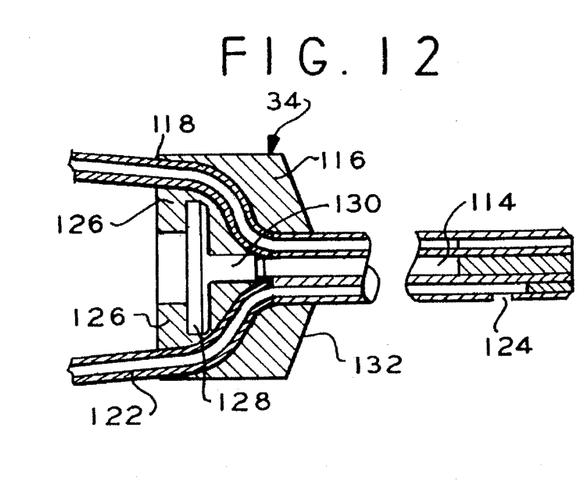
FIG. 12 is a cross-sectional view of the tip along line 12—12 of FIG. 11, with the shaft of the tip omitted for clarity.
Figure 13:
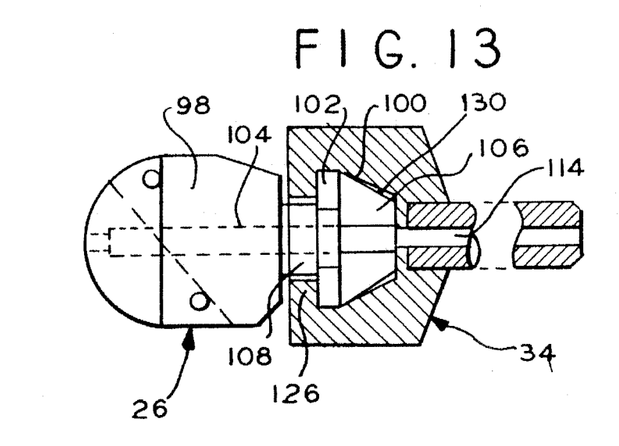
FIG. 13 is a cross-sectional view of the tip along line 13—13 of FIG. 11, showing the snap-drum for receiving the boot of the tip thereon.
Figure 14:
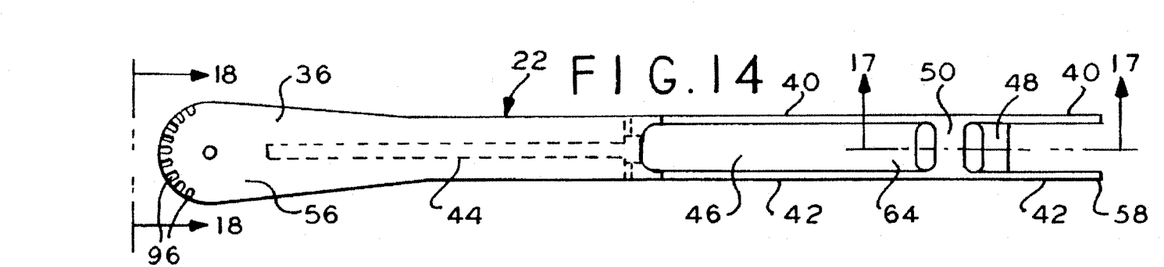
FIG. 14 is a top plan view of the frame of the uterine manipulator, showing the central partition wall in phantom.
Figure 15:
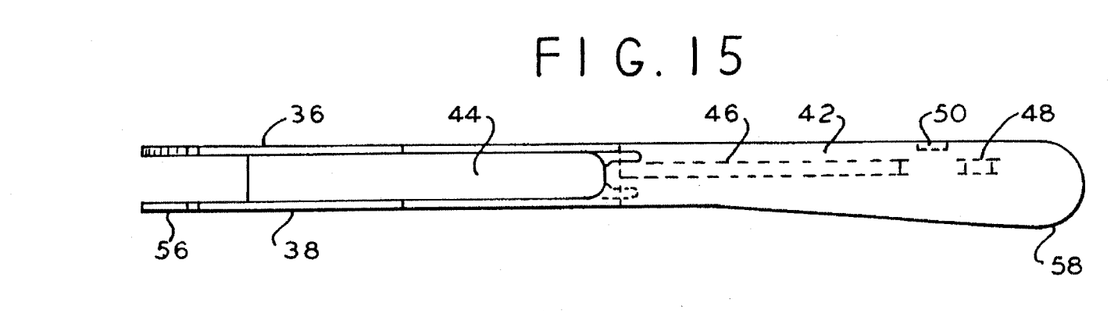
FIG. 15 is a side elevational view of the frame.
Figure 16:
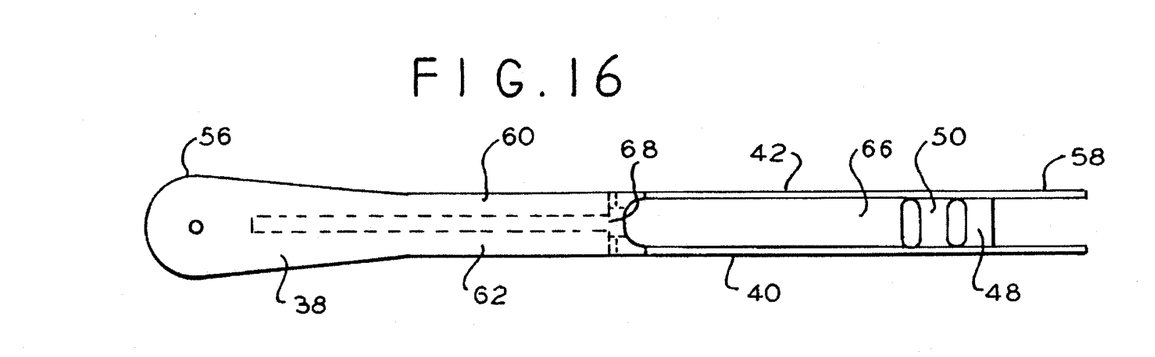
FIG. 16 is a bottom view of the frame.
Figure 17:
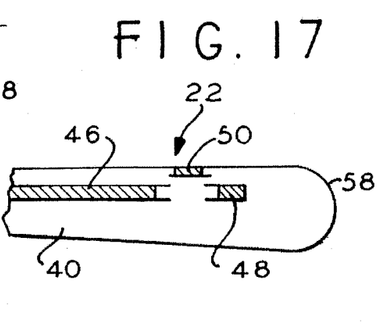
FIG. 17 is a fragmentary vertical sectional view of the frame along lines 17—17 of FIG. 14.
Figure 18:
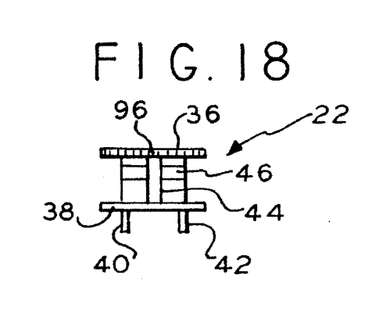
FIG. 18 is a rear end view of the frame of the uterine manipulator of the present invention.

The tip 34 is made of urethane or other flexible synthetic resin material around a rigid metal shaft 114. The shaft 114 extends normally the length of the tip 34 except for the remote end of the tip 34 to permit flexibility of the remote end of the tip, and projects in a proximate or rearward direction to fit into the channel 104. The tip 34 includes a boot 116 of said resilient material which is circular in cross-section as seen in FIG. 11 and receives therein balloon tube 118 which communicates air to a silicone rubber balloon 120 (shown inflated in phantom in FIG. 9). Boot 116 also receives a dye tube 122 which communicates with openings 124a and 124b at the remote end of the tip 34. Because a single opening could be occluded by pressure against the uterine wall during use, the provision of alternate openings 124a and 124b oriented in different directions provides enhanced dye flow capability. Each tube 118 and 122 is provided with the appropriate fittings to connect with respective controlled sources of pressurized air and dye. Boot 116 includes an annular radially inward projecting lip 126 which presents an opening to receive the head 100 of the uterine manipulator therethrough, the lip 126 fitting normally proximate to the head 100 and into the neck 108. Remote to the lip 126 is a circular relieved area 128 which receives the head 100 and is complementally configured, including a remotely projecting slot 130 for receiving the fin 106. The boot 116 thus effectively surrounds the head 100, the boot 116 being provided with a tapered remote surface 132 for ease of insertion into the vaginal cavity.

In use, the physician or nurse will first attach the tip 34 onto the snap-drum 26 of the uterine manipulator and connect the balloon tube to a source of pressurized air, while similarly connecting the dye tube to a source of medical dye as appropriate to the examination. The tip 34 is inserted into the vaginal cavity of the patient until the tip is properly positioned in the patient's uterus. During insertion, the handle 24 may be locked in a position whereby the shaft 114 is substantially aligned with the longitudinal axis of the frame 22 by positioning the catch 94 in the desired notch 96.

Figure 2:
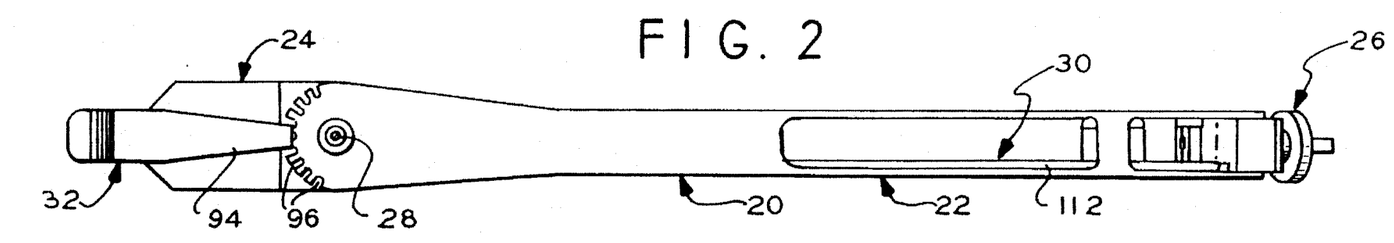
FIG. 2 is a top plan view thereof.

Once inserted, the handle 22 and proximate end of the frame 22 will project from the vaginal cavity. With the patient in a normally supine position with knees elevated, the graspable portion of the handle will be oriented upward. The physician then pivots the handle 24 relative to the frame about a pivot axis defined by the pivot pin 28, the pivot axis thus being parallel to but spaced forwardly or remote from the longitudinal axis of the graspable handle and perpendicular to the longitudinal axis of the frame 22. The preferred range of motion for the snap-drum 26 and tip 34 is about 140° as indicated generally in FIG. 3, with pivoting of the handle 24 to the maximum clockwise position (referring to FIG. 2) reflecting position A and pivoting of the handle to the maximum counterclockwise direction reflection position B. The upright beam 44 impinges on the wires 110 and alternatively 112 at the extreme ranges of motion of the handle 24 relative to the frame 22 and thereby acts as a stop or limit on the range of the tip 34 relative to the frame 22. With the uterus properly positioned, the physician can inflate the balloon 120 to occlude the uterine passage and then inject dye or perform other functions as may be necessary. Advantageously, the handle 22 readily locks in the desired pivoted position unless the physician depresses latch 92 to release the catch 94. Thus, to reposition the tip 34, the physician or nurse depresses the latch 92 on the pawl 90, pivots the handle 24 relative to the frame 22, and releases the latch 92 to lock the tip 34 into the desired orientation. After the procedure is complete, the balloon 120 is deflated, the tip 34 positioned in substantial alignment with the longitudinal axis of the frame 22, and withdrawn.

If the user's hands must be freed during the procedure, a length of gauze or other material may be looped through the central opening 72 in the handle and then the gauze may be tied about the patient's knees or other support to hold the uterine manipulator in position.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state(s) their intent to rely on the Doctrine of Equivalents to determine and assess the reasonably fair scope of their invention as pertains to any apparatus not materially departing from but outside the liberal scope of the invention as set out in the following claims.

We claim:

1. A uterine manipulator comprising:

an elongated frame presenting a proximate end and a remote end and defining a major axis aligned between said ends;

a handle;

means for pivotally coupling said handle to said frame for pivotal movement about a minor axis substantially perpendicular to said major axis;

a drum located at said remote end of said frame;

means for operatively connecting said handle to said drum such that pivoting of said handle produces corresponding articulation of said drum within a predetermined range through a plane substantially parallel to said minor axis; and means for selectively locking said handle against undesired pivoting movement relative to said frame;

said handle including a graspable portion offset to said minor axis for presenting a moment arm when said handle is pivoted relative to said frame.

2. A uterine manipulator as set forth in claim 1, wherein said frame includes structure defining access ports for providing access to said connecting means.

3. A uterine manipulator as set forth in claim 2, wherein said frame includes structure for substantially restricting said connecting means within said frame to provide limited vertical movement of said drum relative to said frame.

4. A uterine manipulator as set forth in claim 3, wherein said connecting means includes a pair of wires, and said restricting structure separates said wires and engages at least respective ones of said wires at least at the limits of said range of articulation.

5. A uterine manipulator as set forth in claim 1, wherein said drum rotatably floats relative to said frame and is held in its floating position by at least one of said frame and said connecting means.

6. A uterine manipulator as set forth in claim 5 wherein the movement of said drum in said plane extends through a range of movement in both retrovert and antevert relationship to said frame.

7. A uterine manipulator as set forth in claim 1, wherein said selective locking means includes a pawl pivotally connected to said handle.

8. A uterine manipulator as set forth in claim 7, wherein said frame includes a plurality of notches for selectively receiving said pawl therein to lock said handle relative to said frame.

9. A uterine manipulator as set forth in claim 8, wherein said pawl is biased toward engagement with said frame.

10. A uterine manipulator as set forth in claim 1, wherein said drum includes a head for mounting a tip thereon, said head including structure for inhibiting axial movement of the tip relative to the head.

11. A uterine manipulator as set forth in claim 10, wherein said drum includes an elongated channel defining a channel axis and said axial movement inhibiting structure includes a rim projecting radially outwardly from the axis of said channel.

12. A uterine manipulator as set forth in claim 1, including a head on said drum and a tip mounted to said head, said tip including a boot of resilient material complementally configured for snap-fitting engagement with said head.

13. A uterine manipulator as set forth in claim 12, wherein said head includes a radially projecting rim and said boot includes a lip for fitting over said rim and a relieved area of dimensions corresponding to said rim.

14. A tip for attachment to a uterine manipulator comprising:

an elongated shaft; and a boot of resilient material connected to said shaft, said boot including structure defining a substantially enclosed recessed area anterior to a substantially annular radially inwardly extending lip for releasably coupling said tip to a uterine manipulator.

15. A uterine manipulator comprising:

an elongated frame presenting a proximate end and a remote end and defining a major axis aligned between said ends;

a handle;

means for pivotally coupling said handle to said frame for pivotal movement about a minor axis substantially perpendicular to said major axis;

a drum located at said remote end of said frame;

means for operatively connecting said handle to said drum whereby pivoting of said handle produces corresponding articulation of said drum within a predetermined range through a plane substantially parallel to said minor axis; and means for selectively locking said handle against undesired pivoting movement relative to said frame;

said selective locking means including a pawl pivotally connected to said handle.

16. A uterine manipulator as set forth in claim 15, wherein said frame includes a plurality of notches for selectively receiving said pawl therein to lock said handle relative to said frame.

17. A uterine manipulator as set forth in claim 16, wherein said pawl is biased toward engagement with said frame.

18. A uterine manipulator comprising:

an elongated frame presenting a proximate end and a remote end and defining a major axis aligned between said ends;

a handle;

means for pivotally coupling said handle to said frame for pivotal movement about a minor axis substantially perpendicular to said major axis;

a drum located at said remote end of said frame; and connecting means for operatively connecting said handle to said drum whereby pivoting of said handle produces articulation of said drum within a predetermined range through a plane substantially parallel to said minor axis;

said frame and connecting means being arranged so that said drum rotatably floats relative to said frame and is held in its floating position by at least one of said frame and connecting means.

19. The uterine manipulator as set forth in claim 18 wherein the connecting means and frame are arranged so that the drum articulation includes rotation and translation.

20. A uterine manipulator comprising:

a frame;

a drum;

a uterine manipulator finger attached to the drum;

said frame including support means for movably supporting the drum; and drive means operatively connected to the drum for articulating the drum, said support means permitting said drum to rotate and translate relative to said frame during said articulation.

21. A uterine manipulator comprising:

an elongated frame presenting a proximate end and a remote end and defining a major axis aligned between said ends;

a handle;

means for pivotally coupling said handle to said frame for pivotal movement about a minor axis substantially perpendicular to said major axis;

a drum located at said remote end of said frame;

means for operatively connecting said handle to said drum whereby pivoting of said handle produces corresponding articulation of said drum within a predetermined range through a plane substantially parallel to said minor axis; and means for selectively locking said handle against undesired pivoting movement relative to said frame;

said drum including a head for mounting a tip thereon, said head including structure for inhibiting axial movement of the tip relative to the head;

said drum including an elongated channel defining a channel axis and said axial movement inhibiting structure includes a rim projecting radially outwardly from the axis of said channel.

22. A uterine manipulator comprising:

a frame;

a drum;

a uterine manipulator finger attached to the drum;

said frame including support means for movably supporting the drum; and drive means operatively connected to the drum for articulating the drum, said support means and drive means being arranged to permit the drum to move the finger in both retrovert and antevert relation to the frame; wherein the support means and the drive means are arranged for causing the drum to rotate and translate relative to said frame during articulation of the drum.

23. The uterine manipulator as set forth in claim 22 wherein the support means and drive means are arranged so that the drum rotates through an angle of up to about 140°.

* * * * *

UNITED STATES PATENT AND TRADEMARK OFFICE
CERTIFICATE OF CORRECTION

PATENT NO. : 5,540,700
DATED : July 30, 1996
INVENTOR(S) : Jimmy M. Rowden, et al It is certified that error appears in the above-indentified patent and that said Letters Patent is hereby corrected as shown below:

Column 7, line 41, after "frame" insert -- to a plurality of positions --.

Column 8, line 14, (claim 14, last line) after "manipulator" insert --; said recessed area including at least one slot for receiving a complementally configured member on said uterine manipulator and for precluding rotational movement of said tip relative to said shaft about an axis coincident with said shaft --.

Signed and Sealed this

Twenty-sixth Day of November 1996

Attest:

BRUCE LEHMAN

Attesting Officer      Commissioner of Patents and Trademarks